(12) United States Patent
Barsuhn et al.

(10) Patent No.: US 6,288,080 B1
(45) Date of Patent: Sep. 11, 2001

(54) MAGNESIUM QUINOLONE ANTIBIOTICS

(75) Inventors: Karen Barsuhn, Plainwell; Ching-Chiang Su, Portage, both of MI (US); Rodney K. Frank, Vadnais Heights, MN (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/197,119

(22) Filed: Nov. 20, 1998

Related U.S. Application Data

(60) Provisional application No. 60/067,829, filed on Dec. 5, 1997.

(51) Int. Cl.[7] .................................................. A61K 31/47
(52) U.S. Cl. .............................................................. 514/312
(58) Field of Search ............................................. 514/312

(56) References Cited

U.S. PATENT DOCUMENTS

| | | | |
|---|---|---|---|
| 4,730,000 | 3/1988 | Chu | 514/254 |
| 4,772,605 | 9/1988 | Naik et al. | 514/254 |
| 5,023,257 | 6/1991 | Pöllinger et al. | 514/254 |
| 5,084,276 | 1/1992 | Yunker et al. | 424/422 |
| 5,225,413 | 7/1993 | Naik | 514/254 |
| 5,290,794 | 3/1994 | Mehta | 514/300 |
| 5,304,559 | 4/1994 | Rozier | 514/255 |
| 5,334,589 | 8/1994 | Al-Razzak et al. | 514/185 |
| 5,425,935 | 6/1995 | Solanki | 424/1.65 |
| 5,563,155 | * 10/1996 | Domagala et al. | 514/312 |

FOREIGN PATENT DOCUMENTS

| | | |
|---|---|---|
| 3635062 | 4/1988 | (DE) . |
| 2 010 633 | 11/1989 | (ES) . |
| WO 91/09525 | 7/1991 | (WO) . |
| WO 93/05816 | 4/1993 | (WO) . |
| WO 94/22075 | 9/1994 | (WO) . |
| WO 9426110 | 11/1994 | (WO) . |

OTHER PUBLICATIONS

JS Chapman, et al, Antimicrobial agents and chemotherapy, 32,(4) "Routes of Quinolone Permeation in *Escherichia coli*" pp. 438–442 (1988).

A. Cole., et al., *Inorganica Chimica Acta*, 92, "The Complexation of Transition Series Metal Ions by Nalidixic Acid" pp. 91–97 (1984).

S. Valiseana, et al., *Biochemical Pharmacology*, 40, "Relevance of Ionic Effects on Norfloxacin Uptake by *Escherichia Coli*," pp. 431–436 (1990).

JT Smith and NT Ratcliffe, "Effect of pH and magnesium on the in vitro activity of ciprofloxacin".

Danna L. Ross and Christopher M. Riley, *International Journal of Pharmaceutics*, 93, pp. 121–129 (1993).

E. Escribano, et al., *Antimicrobial Agents and Chemotherapy*, pp 1996–2000 (1997).

* cited by examiner

*Primary Examiner*—Kevin E. Weddington
(74) *Attorney, Agent, or Firm*—Woodcock Washburn Kurtz Mackiewicz & Norris, LLP

(57) ABSTRACT

Unique Mg-quinolone complexes are disclosed. They are relatively highly soluble, they may exist as a solution without a precipitate forming and without any need for additional acid or base additions to adjust pH, they may be administered as a subcutaneous or intramuscular injection with a low injection site irritation profile, and they are rapidly absorbed and taken up into the bloodstream.

15 Claims, 2 Drawing Sheets

MAGNESIUM QUINOLONE ANTIBIOTICS

CROSS-REFERENCE TO RELATED APPLICATIONS

This application claims the benefit of U.S. provisional application Ser. No. 60/067,829 filed Dec. 5, 1997, under 35 USC §119(e)(i) and PCT application Ser. No. PCT/US98/24525 filed Nov. 23, 1998, under 35 USC §120.

FIELD OF THE INVENTION

This invention is related to the field of quinolone antibiotics and involves the use of Mg2+ ions plus an antibiotic quinolone to create a superior injectable formulation.

INFORMATION DISCLOSURE

U.S. Pat. No. 4,730,000, issued Mar. 8, 1988. Chu, Daniel T., "Quinoline Antibacterial Compounds."

U.S. Pat. No. 4,772,605 issued Sep. 20, 1988. Naik, Arundev H., et al. "Basic Formulations of Quinolonecarboxylic Acids."

U.S. Pat. No. 5,023,257 issued Jun. 11, 1991. Pöllinger, N., et al., "Intramuscular Injection Forms of Gyrase Inhibitors."

U.S. Pat. No. 5,084,276 issued Jan. 28, 1992. Yunker, Martin H., et al., "Quinolone Carboxylic Acid Compositions with Polymeric Additive to Reduce Vein Irritation."

U.S. Pat. No. 5,225,413 issued Jul. 6, 1993. Naik, Arundev H., "PH-Neutral Aqueous Solutions of Quinolone-Carboxylic Acids."

U.S. Pat. No. 5,290,794 issued Mar. 1, 1994. Mehta, Surendra C., et al., "Soluble Calcium Lactate Antibacterial Complexes as Non-Irritating Parenteral Forms."

U.S. Pat. No. 5,304,559 issued Apr. 19, 1994. Rozier, A., "Compositions Containing a 4-Quinolone Derivative Complexed with a Divalent Metal Ion."

U.S. Pat. No. 5,334,589 issued Aug. 2, 1994. Al-Razzak, L. A., et al., "Quinolone Carboxylic Acid-Metal Ion-Acid Complexes."

U.S. Pat. No. 5,425,935 issued Jun. 20, 1995. Solanki, K. K., "Imaging of Infections."

International Publication No. WO91/09525 published Jul. 11, 1991. Al-Razzak, L., et al., "Quinolone Carboxylic Acid-Metal Ion-Acid Complexes."

International Publication No. WO93/05816 published Apr. 1, 1993. Yusuf, A., et al., "Compositions Containing Quinolone Antibiotics and Sulfonate of Polystyrol."

International Publication No. WO94/20075 published Sep. 15, 1994. Derrieu, G., et al., "Controlled Release Microcapsules, Process for their Preparation and Pharmaceutical or Veterinary Compositions Containing Same."

International Publication No. WO94/26110 published Nov. 24, 1994. Gupta, P. K., et al., "Stable Quinolone and Naphthyridine Premix Formulations."

Spanish Patent ES 2 010 633 published Nov. 16, 1989. López Molina, Isidro, et al.,.

German Patent DE 3635062 published Apr. 21, 1988. Grohe, K.

Chapman, John S., et al., *Antimicrobial agents and chemotherapy*, 32,(4) "Routes of Quinolone Permeation in *Escherichia coli*," pp. 438–442 (1988).

Cole, A., et al., *Inorganica Chimica Acta*, 92, "The Complexation of Transition Series Metal Ions by Nalidixic Acid," pp. 91–97 (1984).

Valiseana, S., et al., *Biochemical Pharmacology*, 40, "Relevance of Ionic Effects on Norfloxacin Uptake by *Escherichia Coli*," pp. 431–436 (1990).

Smith, J. T. and Ratcliffe, N. T., "Effect of pH and magnesium on the in vitro activity of ciprofloxacin."

Ross, Danna L. and Riley, Christopher M., *International Journal of Pharmaceutics*, 93, pp 121–129 (1993).

Escribano, E., et al., *Antimicrobial Agents and Chemotherapy*, pp 1996–2000 (1997).

BACKGROUND

Fluoroquinolone derivatives are well known for their inhibitory activity on the synthesis of bacterial deoxyribonucleic acid, and consequently are good bactericides. Most fluoroquinolones are also poorly soluble in water and poor aqueous solubility of a drug can make it difficult to deliver that drug in an efficacious manner to a patient. Researchers have made various attempts to either improve the aqueous solubility of fluoroquinolones or to create suspensions of fluoroquinolone drug that can then be delivered to a patient. For example, U.S. Pat. No. 5,304,559 suggests the use of a divalent metal ion such as Cu++, Zn++, or Mg2+ and acids, to create salts that are then maintained as stable suspensions for use as parenteral or more preferably as ophthalmic formulations. U.S. Pat. No. 5,225,413 recommends the use of calcium ions and adjusting the pH to 6.5 to 7.5 to create a water soluble solution of quinolone that can be used for egg dipping.

Quinolone carboxylic acid—metal ion—acid complexes are described in U.S. Pat. No. 5,334,589 to describe compositions of quinolone carboxylic acids plus metal ions plus acid to form an acid complex that can then be used in intravenous administrations. As an added benefit, this quinolone—metal ion—acid complex is also said to have decreased venous irritation upon injection. In contrast to this suggestion, others have reported that divalent metal ions, in particular Mg2+ ions, have a pronounced inhibitory effect on an animal's uptake of quinolone, apparently the metal ion complex reduces the bioavailability of quinolones. See, S. Valisena, et. al. "Relevance of Ionic Effects on Norfloxacin Uptake by *E. Coli*." Biochemical Pharmacology, vol. 40. no. 3, pp. 431–436 (1990) and John S. Chapman and Nafsika H. Georgopapadakou, "Antimicrobial Agents and Chemotherapy," vol 32. no. 4, pp. 438–442, (1988).

This disclosure provides novel quinolone complexes with surprising and unexpectedly improved properties over previously disclosed compositions.

SUMMARY OF THE INVENTION

Unique Mg-quinolone complexes are disclosed. They are relatively highly soluble, they may exist as a solution without a precipitate forming and without any need for additional acid or base additions to adjust pH, they may be administered as a subcutaneous or intramuscular injection with a low injection site irritation profile, and they are rapidly absorbed and taken up into the bloodstream.

This invention comprises selected quinolones described in U.S. Pat. No. 5,563,155, combined with Mg. More specifically, the quinolones described in U.S. Pat. No. 5,563,155, in solution, with Mg2+ ions, in a range from ratios of 1:4 to 3:1 parts of Mg2+ ion to quinolone. With ratios of 1:1 and 2:1 being more preferred embodiments and a ratio of 2:1 Mg2+ ion to quinolone being the most preferred embodiment with the more preferred quinolones being 8 position cyclopropyl derivatives and most preferred is 3R, 1S-1- cyclopropyl-7-(3(1-(methylamino)ethyl)-1-pyrrolidinyl)-6-fluoro-1,4-dihydro-8-methoxy-4-oxo-3-quinolinecarboxylic acid, see, Formula 1, and its esters, in the form of the zwitterion, also disclosed in claim 8 of U.S. Pat. No. 5,563,155, incorporated by reference. Methods of preparing the complexes, methods of using them to treat animals and methods of preparing medicaments are all disclosed.

BRIEF DESCRIPTION OF THE DRAWINGS

FIG. 1 shows data from time 0 to 12 hours.

FIG. 2 shows from time 0 to 48 hours.

ADDITIONAL DETAILS OF THE INVENTION

Figure 1:
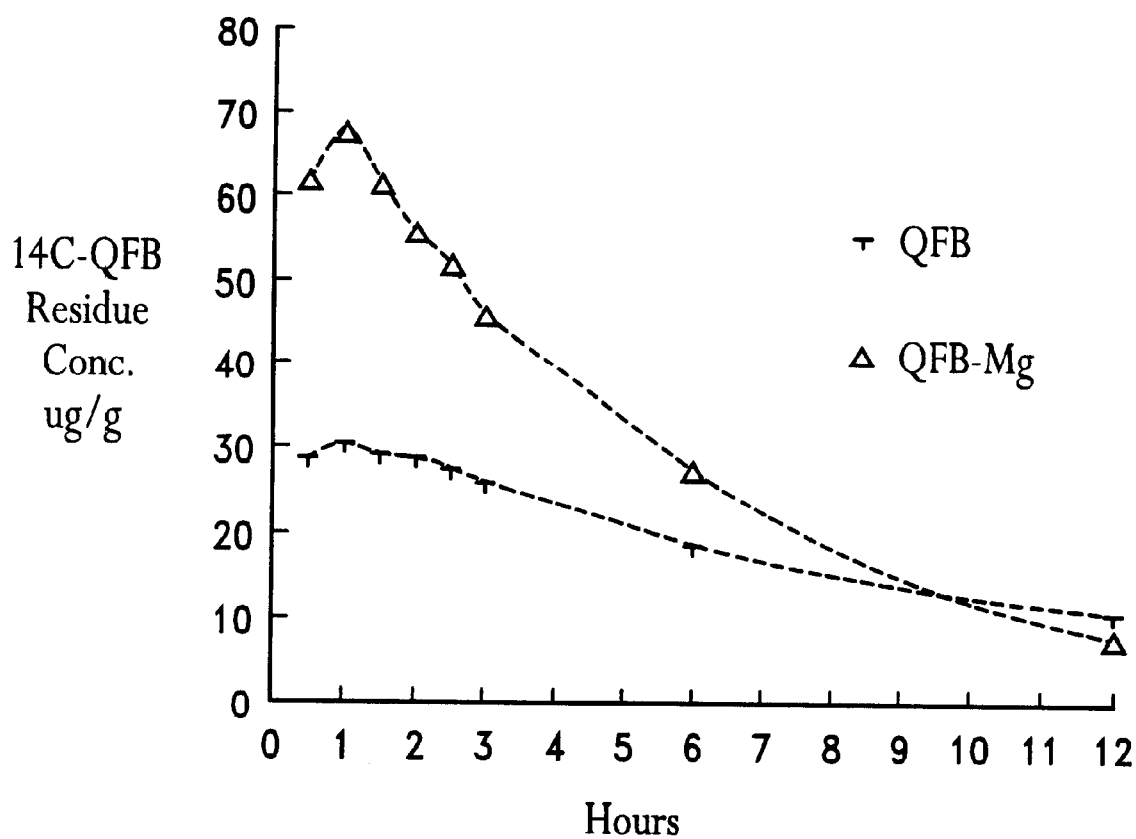
FIG. 1. Shows the serum depletion profile in two treatment groups of calves following subcutaneous administration of radiolabeled 14C-quinolone with and without magnesium.

In this document the ionic form of magnesium and magnesium may be represented in a variety of ways. Typically the ionic form is shown as Mg2+, it may also be Mg+2, or Mg++ or no charge may be indicated. The charges indicated, +2, 2+ or ++, may be in superscript but more often they are not. Mg is also magnesium and if used alone it indicates either ionic form or neutral form with the counter ion not indicated. If Mg is shown with a counter ion, such as in $MgCl_2$, then the counter ions may be in solution or they may exist in solid form.

Most quinolone antibiotics have low aqueous solubilities, see Ross, Danna L. and Riley, Christopher M., "Aqueous Solubility of Some Variously Substituted Quinolone Anti-Microbials." *International Journal of Pharmaceutics*, vol. 63, pp. 237–250 (1990). Typically, when aqueous solutions of quinolone antibiotics are used, they are low concentration solutions that are administered intravenously as infusions to treat humans. Here are the intrinsic solubilities at 25° C. according to Ross and Riley, id. Amifloxacin—0.187 M $10^{-3}$, Ciprofloxacin—0.238 M $10^{-3}$, Difloxacin—0.153 M $10^{-3}$, Enofloxacin—1.19 M $10^{-3}$, Fleroxacin—1.88 M $10^{-3}$, Lomefloxacin—2.93 M $10^{-3}$, Nalidixic acid—0.128M $10^{-3}$, Norfloxacin—1.00 M $10^{-3}$, Ofloxacin—7.64 M $10^{-3}$, Temafloxacin—0.158 M $10^{-3}$. Id. This type of administration is not practical for a typical veterinary administration of an antibiotic. A good veterinary formulation of a drug requires something that can be administered quickly and preferably just once. This presents a problem for most quinolones because of their low solubility. Other formulations are possible. For example, a suspension or a precipitated solution is an undissolved mixture of crystals "suspended" in a liquid. Gravity will cause the suspended crystals to gradually fall to the bottom of the liquid, but the suspension can be shaken before injection. Conversely, solutions are clear liquids, which may contain dissolved compounds. Compounds dissolved in solutions usually do not "precipitate out" of solution unless the concentration of the compounds in solution exceeds the solubility concentration. Quinolone antibiotics typically have low aqueous solubility and form precipitates due to settling of the undissolved drug rather than forming true solutions of dissolved compound in concentrations high enough to be suitable for administration to an animal or human patient via a single injection.

The inventors here have discovered that an unusual type of quinolone can be combined with Mg2+ ions to produce a unique and surprisingly effective injectable quinolone formulation. The inventors have also discovered that not only do the Mg2+ ions reduce injection site irritation but they significantly increase the aqueous solubility of the quinolones. It appears the predominate complexes are complexes with a ratio of 4:1 (drug:ion) complex but ratios of 3:1 and 2:1 are also possible.

The compounds disclosed in U.S. Pat. No. 5,563,155, ('155) are incorporated by reference here to fully disclose and enable this invention. The following compounds of the '155 patent are pointed out and particularly incorporated here. Those compounds in U.S. Pat No. 5,563,155, ('155) having relatively high solubility (greater than 2 mg/ml) in water. More particularly disclosed by incorporation by reference are those compounds of '155, in claim 1, where $R_2$ is H and where R or R' is H. The quinolone where $R_2$ is H and where R or R' is H can be combined with Mg2+ ions to produce a soluble complex having reduced injection site irritation. More preferred are the compounds of '155, in claim 1, where $R_2$ is H and where R or R' is H, and where $R_3$ is H and X is C—O—$CH_3$. The esters of these compounds are also disclosed herein, the carboxy esters of 1–8 carbon groups are disclosed here, including all isomeric combinations ($CH_3$, $C_2H_5$, $C_3H_7$, $C_4H_9$, $C_5H_{11}$, $C_6H_{13}$, $C_7H_{15}$, $C_8H_{17}$— both straight and branched chains) and especially preferred are the carboxy esters of 1–4 carbon groups such as in U.S. Pat. No. 5,563,155, claim 1, where $R_2$ is an alkyl of 1–4 carbon atoms or a cation. Even more preferred are the compounds of claim 2, most particularly the compound of claim 8 or 3R,1S-1-cyclopropyl-7-(3-(1-(methylamino)ethyl)-1-pyrrolidinyl)-6-fluoro-1,4-dihydro-8-methoxy-4-oxo-3-quinolinecarboxylic acid. This latter specific compound has an estimated intrinsic solubility at 25° C. of about 2.2 mg/ml. Also, particular attention is directed to the descriptions in the specification of the '155 patent that correspond or are relevant to those claims and compounds described here.

The quinolones mentioned above can exist in different forms, the different forms having different solubilities. For example 3R,1S-1-cyclopropyl-7-(3-(1-(methylamino) ethyl)-1-pyrrolidinyl)-6-fluoro-1,4-dihydro-8-methoxy-4-oxo-3-quinolinecarboxylic acid can exist in a more soluble form known as Form 1 with a solubility of about 10.8 mg/ml or it can exist in a less soluble form known as Form 3 with a solubility of about 2.2 mg/ml. Even though it is the less soluble crystal form, Form III is very suitable as the quinolone that may be combined with Mg2+ in this invention. See, WO96/16055, incorporated by reference. As an overall commercial injection formulation, the Form III may even be preferable to Form I. Forms having lower solubility but greater stability are also described, thus Mg-Quinolones having solubility's of at least 1.0 mg/ml at 25° C. are thus disclosed, as are those with solubility's of at least 2.0 mg/ml at 25° C., 2.2 mg/ml at 25° C., and 10.8 mg/ml at 25° C.

Unfortunately these compounds also produce a severe adverse reaction at the injection site when injected subcutaneously in animals. This injection site irritation, and particularly that from 3R,1S-1-cyclopropyl-7-(3-(1-(methylamino)ethyl)-1-pyrrolidinyl)-6-fluoro-1,4-dihydro-8-methoxy-4-oxo-3-quinolinecarboxylic acid, here, the quinolone, Formula 1, the zwitterion and the free base form, can involve dramatic swelling, discoloration, internal and external lesions and even necrosis.

The inventors here have discovered that it is possible to greatly reduce the unpleasant side effects from injection of this water soluble quinolone by making a solution of the quinolone with magnesium ions (Mg2+). These Mg-quinolone aqueous complexes create quinolone solutions that have the dual properties of being a fairly concentrated aqueous solution of quinolone plus they have a greatly reduced injection site irritation profile when compared to solutions without the Mg2+ ions. The solutions created here result in superior formulations than solutions of the quinolone and other metal ions, or when compared to solutions of the quinolone and many organic acids.

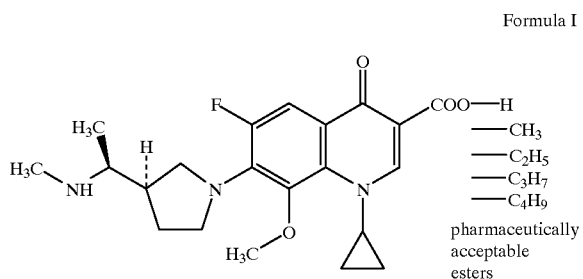

Formula I

Formula I

The compounds that may be made into solutions of this type are those compounds disclosed in Formula 1 and in U.S. Pat. No. 5,563,155, incorporated herein by reference and particularly 3R,1S-1-cyclopropyl-7-(3-(1-(methylamino)ethyl)-1-pyrrolidinyl)-6-fluoro-1,4-dihydro-8-methoxy-4-oxo-3-quinolinecarboxylic acid. Compared to most quinolones, the quinolones preferred here have unusually high water solubilities. For a comparison see Ross & Riley, *International Journal of Pharmaceutics*, vol.63 pp.237–250, 1990, particularly page 246. This article shows that, at physiological pH, most quinolones have solubilities of less than 1 mg/ml, although Ross did find one quinolone with a solubility of about 3.23 mg/ml. The quinolones disclosed here have solubilities of from 2.2 to 10.8, depending upon the crystal form. When the quinolones disclosed in this document are combined with $MgCl_2$ in solution one obtains an aqueous quinolone formulation having a surprisingly high concentration of quinolone that is suitable for administration by parenteral infection.

A good method of making the quinolone-Mg solutions disclosed here is to mix the water with the quinolone first, creating a suspension, then adding the $MgCl_2$, followed by agitation, such as shaking or stirring, to dissolve the ingredients, making a clear solution. Adding $MgCl_2$ to water and then adding quinolone will also create a solution after agitation, but a solution is created easier and quicker if the $MgCl_2$ is added after the quinolone is first mixed with the water.

In addition to the beneficial properties of high solubility and decreased injection site irritation, the compositions of this invention have the additional beneficial property of apparently having rapid clearance or movement of the drug from the injection site to systemic dispersal in an animal. This movement suggests the compound is more rapidly delivered to the site of infection than if it remained localized at the injection site, another surprising and beneficial result. These results suggest the compositions described here may have a significant increase in the rate of absorption of the quinolone-Mg complex at the injection site when compared to animals receiving the quinolone alone. In addition, the residue concentration at the injection site is much lower and depletes faster in animals injected with the quinolone-Mg complex compositions compared to residue concentrations from injections of quinolone alone.

Perhaps most surprising, we have discovered that with the Mg2+ solutions disclosed herein, the concentration of quinolone in the blood stream of treated animals is much higher than quinolone concentrations in the blood of animals treated with quinolone but without the Mg2+ solutions. Preliminary results with a compound of Formula I indicate the average increase in blood concentration of animals (CMAX—maximum concentration) treated with the Mg2+ solutions is twice that of animals treated with solutions of quinolones without Mg2+. A higher blood concentration of quinolone can mean more effective bacterial control. If one considers the maximum concentration (CMAX) to MIC (minimum inhibitory concentration) of the target organism, the averages of the ratios of these numbers both approximately double for Mg2+ solutions as compared to similar solutions without Mg2+. CMAX/MIC is a surrogate marker for the potential to cause resistance and a surrogate for efficacy. As ratios of CMAX/MIC increases the potential for development of resistance decreases, but the efficacy increases. Typically metal complexes with quinolones decrease blood levels when compared to the noncomplexed form, here we see the opposite effect with the Mg2+ solutions.

The optimal molar ratio of Mg to quinolone seems to be about 2:1, a ratio of 1:1 is also suitable, but ratios of anywhere from 1:4 through 3:1 (including 1:4, 1:2, 1:1, 2:1, 3:1) of Mg to quinolone all produce complexes having the surprising properties of good aqueous solubility with lower injection site irritation profiles.

When high ratios of Mg:drug are used, particularly at high drug concentrations, the solutions can have rather high levels of Mg and Cl ions and yet there is good bioavailability. A surprising result in view of the fact that other quinolones in combination with di- and trivalent cations are reported to have reduced bioavailability. In addition, the high ionic strength of the solutions with high Mg:drug ratios disclosed here would probably not be amenable to the addition of additional acid or base buffering agents. Here those agents are not needed due to the natural (near) neutral pH of the solution.

The solutions here can also be used with preservatives commonly used in the industry. Preservatives are placed in sterile solutions to prevent or control the growth of bacteria and to keep solutions in condition suitable for injection. With this invention most preservatives are suitable but the following are especially suitable, benzyalkonium chloride, which provides good ionic compatibility, benzyl alcohol and m-cresol. The quinolone-Mg solutions may also be autoclaved under conditions of high temperature and pressure for sterilazation without loss of potency.

Without any further description it is believed the foregoing provides a complete and detailed description of the invention. The following detailed descriptions of particular embodiments of this invention, and the included descriptions of a representative comparison showing the advantages of the disclosed invention is provided to illustrate and not to limit the invention in any way.

The following experiments and results are provided. In all of the experiments below when reference is made to "the quinolone," "quinolone free base," "QFB" or similar such designations to a particular quinolone, the specific quinolone that is being referred to has the chemical name [S-(R*,S*)]-1-Cyclopropyl-6-fluoro-1,4-dihydro-8-methoxy-7-[3-[1-(methylamino)ethyl]-1-pyrrolidinyl]-4-oxo-3-quinolinecarboxylic acid. This is the same compound named and described above, structure provided as Formula 1, acid. In the experiments below, h or hr. is hour, g or gm. is gram, L is liter and mL is milliliter.

It should be understood that when reference is made to the quinolone-Mg or Mg-quinolone or $Mg^{2+}$-quinolone solutions that the quinolone itself will likely be in the zwitterion form. When the specification refers to the terms "Quinolone as Free Base" or "QFB" as for example in Experiment 4, when referring to the Mg formulations, it is in fact most likely the zwitterion form and not the free base form.

The word "rank" or "ranked" indicates that the measurements or scores for each test group were placed in order or sorted from lowest to highest. The group with the lowest score was assigned a value of 1, the next a value of 2, etc. These rank order values were then summed across all of the variables to obtain the 'Rank Sum Score' (RSS) for each test group. The test group with the lowest RSS was the least irritating and the group with the highest score was the most irritating.

Rat irritation model. Groups of three adult male or female Crl:CD(SD)BR Sprague-Dawley rats received one of the experimental formulations or vehicle at four unique predetermined sites/rat.

Method of Administration: Each rat had four shaved sites (one on each side of the thorax and one on the right lateral abdominal area) which were shaved one day prior to dose initiation. Each of three sites received a single, unique subcutaneous injection of an experimental formulation, while the fourth received the respective vehicle.

Dose Volumes: 0.04 mL, 0.08 mL and 0.2 mL per injection site. All test articles were subcutaneously injected using a separate 26 gauge ×½" hypodermic needle for each site.

Injection sites evaluation: Injection sites were evaluated approximately 24 and 48 h postinjection (PI). Parameters evaluated were 24 and 48 h PI measurements of external lesion size, 24 and 48 h PI subjective scoring of lesion severity. At approximately 48 h PI, the rats were sacrificed and subjected to an abbreviated necropsy which consisted of measurements of the internal lesions and a subjective characterization of the lesion severity. A sum of the ranked scores was calculated using the ranks of the scores for all the various irritation categories (48 h irritation scores (0.2 mL, 0.08 mL and 0.04 mL sites), 48 h external lesion size, and internal lesion volumes (0.2 mL, 0.08 mL, and 0.04 mL sites)) to compare the irritancy (tolerance) of the formulations within an experiment. For comparisons across experiments, Total Irritation Score (TIS) was calculated by summing the 48 h Irritation Scores and the internal lesion volumes for the 0.2 mL injection sites.

Cattle irritation model. Three Holstein cattle (males and females) weighing approximately 300 kg at 9–14 months of age each received subcutaneous injections of the test formulations at eight unique predetermined sites.

Method of Administration: Each of eight sites (3 sites over each side of the thorax and 1 site on each side of the neck) received a single, unique subcutaneous injection of an experimental formulation. Sites were shaved and scrubbed with disinfectant immediately prior to dose initiation.

Dose Volumes: The injection volumes were based on therapeutic dose of 3 mg/kg per injection site and were dependent on the concentration of the test formulation. All test articles were subcutaneously injected using a separate 18 gauge×1½" hypodermic needle for each site.

Injection Site Evaluations: Evaluation of the injection sites was conducted once pretest at the time of shaving. During the study, observations were recorded once daily on day 1–9 PI. Cattle were euthanized 9 days PI and internal lesions were measured and characterized. External injection site irritation scores: 0=normal, 1=palpable swelling, 2=visible (swelling or discoloration) with or without palpability, 3=crusty, scabbed or draining lesion. Internal injection site severity scores: 0=normal, 1=minimal lesion (small area of discoloration with no indication of swelling, no adhesion of dermis to muscle fascia and no dark red areas), 2=mild (small area of discoloration with slight swelling, but no adhesion of dermis to muscle fascia, and no dark red areas), 3=moderate (moderately-sized area with some swelling, slight adhesion of dermis to muscle fascia and one or more areas of dark red), and 4=severe (large area of swelling, predominant adhesion of dermis to muscle fascia, dark red discoloration and evidence of epidermal/dermal necrosis).

Experiment 1. Three groups of rats received the quinolone in conjunction with three different acids (citric, lactic and glucuronic), while three other groups received quinolone in conjunction with three metal ions ($Mg^{2+}$, $Mn^{2+}$ and $Ca^{2+}$).

Formulations: Six formulations of quinolone (at a concentration of 16 mg/mL free base equivalents) were prepared by dissolving 400 gm of bulk drug to 25 mL with 0.04 M acid solutions (citric, lactic or glucuronic) or 0.02 M metal ion solutions ($Mg^{2+}$, $Mn^{2+}$ or $Ca^{2+}$). NaCl was added to adjust the solution tonicity. Solutions were sterile filtered.

Treatment Groups: There were six treatment groups with three male rats, 15 weeks of age per group; each group received one of the six formulations. Each rat received four subcutaneous injections of the formulation for its group. The left side of the thorax received a single 0.2 mL injection, the right side received a single 0.08 mL injection and the third site (right lateral abdominal area) received a single 0.04 mL injection. A fourth subcutaneous site (left lateral abdominal area) received a single 0.20 mL injection of the respective vehicle.

Clinical and Gross Observations: Group mean irritation scores and external lesion or swelling sizes at 24 and 48 h postinjection (PI) were lower for the 0.2 mL sites injected with the combination of 16 mg/mL quinolone and $Mg^{2+}$ and $Mn^{2+}$ than for the sites injected with 16 mg/mL quinolone with citric acid (CA), lactic acid (LA), glucuronic acid (GA) or $Ca^{2+}$. Only occasional palpable swelling was detected at sites injected with 0.08 mL of the various formulations except for one site given quinolone with CA where there was also visible swelling. No visual or palpable lesions were detected at any of the sites injected with 0.04 mL of the formulations. Group mean external lesion sizes were similar for the quinolone formulations containing CA, LA and GA. External lesions (skin necrosis) were not seen at sites given the quinolone formulations containing $Mg^{2+}$ and $Mn^{2+}$. Group mean internal lesion volumes (Table 1) for the 0.2 mL sites injected with the quinolone/$Mg^{2+}$, quinolone($Ca^{2+}$ and quinolone/GA combinations were approximately one-third to one-half the volumes for the other formulations. The quinolone/CA formulation, and the quinolone/$Mn^{2+}$ formulation had the largest lesion volumes for the 0.2 mL sites. Most internal lesions irrespective of formulation were dark red, purple or pink. Edema was seen at one or more of the sites for each formulation. Group mean internal lesions were similar for all of the formulations at the 0.08 mL sites. For the 0.04 mL sites, no internal lesions were seen at any of the sites injected with the quinolone/$Mg^{2+}$ or quinolone/$Mn^{2+}$ and group mean internal lesion volumes were similar for the other sites. The sum of ranked scores was markedly less for sites given the quinolone/$Mg^{2+}$ combination than for the other formulations; sum of ranked scores for the quinolone/$Mn^{2+}$ sites were intermediate and scores for all of the other formulations were similar or higher. At 24 and 48 h PI, all of the vehicle injected sites were normal. No external lesions were seen at any of the sites injected with LA, GA or $Ca^{2+}$, very small lesions (mean volume <0.01 cm3) were seen in 1/3 rats injected with $Mg^{2+}$ and 2/3 rats injected with CA.

Mean lesion volume of the $Mn^{2+}$ injected rats was 0.12 cm3 due to lesion seen in 1/3 rats.

Table 1 provides additional or summary information about the results of this experiment.

TABLE 1

Experiment 1
Observed and summary results 0.2 mL injection sites (triplicate)

| Formulation (16 mg/mL) | Mean 48 Hr Irritation Score | Mean Internal Lesion volume cm³ | TIS | Sum of Rank Score |
|---|---|---|---|---|
| $Mg^{2+}$ | 1.67 | 0.18 | 5.55 | 6 |
| $Mn^{2+}$ | 1.67 | 0.72 | 7.17 | 13 |
| Glucuronic Acid | 2.00 | 0.21 | 6.64 | 20 |
| Lactic acid | 2.67 | 0.40 | 9.19 | 23 |
| Citric Acid | 2.67 | 0.54 | 9.62 | 27 |
| $Ca^{2+}$ | 3.00 | 0.21 | 9.64 | 28 |

TIS is Total Irritation Score.

Experiment 2. Five groups of rats received the quinolone formulated as solutions (with $Mg^{2+}$ or $Mg^{2+}$ lactic acid) or as suspensions/emulsions.

Formulations: Five formulations of quinolone (at a concentration of 16 mg/mL free base equivalents) were prepared by dissolving 400 gm of bulk drug to 25 mL with 0.02 M $MgCl_2$ or 0.01 M $MgCl_2$ +0.01 M lactic acid; LA. NaCl was added to adjust the solution tonicity and the solutions were sterile filtered. The other formulations were prepared by suspending 400 gm of bulk drug in 25 mL of the respective vehicle with mechanical agitation. Vehicles included a cottonseed oil based vehicle (CV), an aqueous vehicle containing CMC (A) and an soybean oil based emulsion (Intralipid 10%; IL). Also included was a competitor fluoroquinolone product (DX). DX is danofloxacin. CMC is carboxymethylcellulose.

Treatment Groups: There were five treatment groups with three male rats per group, 18 weeks of age per group; each group received one of the five formulations. Each rat received four subcutaneous injections of the formulation for its group. The left side of the thorax received a single 0.2 mL injection, the right side received a single 0.08 mL injection and the third site (right lateral abdominal area) received a single 0.04 mL injection. A fourth subcutaneous site (left lateral abdominal area) received a single 0.20 mL injection of the respective vehicle.

Clinical and Gross Observations: Group mean Irritation Scores (48 hr PI; Table 2) were lower for the 0.2 mL injected sites with premafloxacin in combination with Mg and CV <Mg+LA and A or IL. The lowest mean irritation score was seen with the competitor product DX Only one site given the IL formulation (0.2 mL) had an external lesion (skin necrosis). All vehicle injected sites were normal (DX vehicle was not available).

Sites injected with premafloxacin-Mg had the smallest lesion volumes and none were dark red (the most severe type of lesion associated with fluoroquinolone injections). The largest lesion volumes were seen with the Mg+LA and IL formulations with dark red lesions seen at 2/3 and 1/2 sites, respectively. No internal lesions were seen at any of the 0.08 or 0.04 mL injection sites with the Mg formulation. Lesions were seen at 3/3 of the sites given 0.08 mL of A, Mg+LA and DX and 2/3 sites for each formulation had dark red lesions. For the 0.04 mL injections, no internal lesions were seen at any of the sites injected with CV; at 2/3 sites given Mg+LA, IL and DX; and 1/3 sites given A. No irritation/lesions were seen at any of the respective vehicle injection sites.

TABLE 2

Experiment 2
Observed and summary results 0.2 mL injection sites (triplicate)

| Formulation (16 mg/mL) | Mean 48 Hr Irritation Score | Mean Internal Lesion volume cm³ | TIS | Sum of Rank Score |
|---|---|---|---|---|
| $Mg^{2+}$ | 1.00 | 0.12 | 3.37 | 8 |
| CV | 0.67 | 0.38 | 6.50 | 14 |
| DX | 0.33 | 0.15 | 1.45 | 18 |
| IL | 2.00 | 0.74 | 8.21 | 18 |
| $Mg^{2+}$ LA | 1.33 | 0.45 | 5.35 | 23 |
| A | 2.33 | 0.23 | 7.70 | 32 |

TIS is Total Irritation Score.

Experiment 3. Quinolone (at a concentration of 16 or 25 mg/mL) was subcutaneously dosed in conjunction with $Mg^{2+}$, citric acid, as an oil suspension or as an emulsion.

Formulations: Solution, suspension and emulsions of quinolone were prepared by adding 400 gms (16 mg/mL) or 655 gms (25 mg/mL) of bulk drug into 25 mL of the designated vehicle. Solutions were prepared from Citric acid (0.04 and 0.06 M; CA) and $MgCl_2$ (0.02 and 0.03 M; $MgCl_2$); the suspension was prepared with a cottonseed oil vehicle (CV); and the emulsion was prepared with Intralipid 10% (IL). The aqueous solutions were adjusted for tonicity with NaCl and were sterile filtered.

Treatment Groups: There were two treatment groups with each group having three female rats, 11 weeks of old. One group received 16 mg/mL quinolone and the other 25 mg/mL quinolone. Each group received the same concentration of each of the four formulations at a volume of 0.20 mL. Each rat received four subcutaneous injections (one on each side of the thorax and one on each side of the lateral abdominal area) of the four formulations for its group.

Clinical and Gross Observations: Irritation scores were similar for all four formulations at both quinolone concentrations (16 and 25 mg/mL) at 24 and 48 h PI and were characterized by crusty scabbed external lesions. Mean external lesion scores 48 h postinjection (PI) and group mean internal lesion volumes are shown in Table 2. Mean external lesion sizes were similar for the 25 mg/mL CV and Mg formulations and the 16 mg/mL Mg and IL formulations (1.10–1.23 cm²). ranged from 0.02 (Mg; 16 mg/ml quinolone)–1.41 (IL; 25 mg/mL quinolone) cm³. The Mg formulations produced the smallest lesion volumes at both 16 and 25 mg/mL quinolone. Two of these 16 mg/mL quinolone sites for the Mg formulations produced no grossly visible internal lesions.

Discussion: The quinolone/Mg and quinolone/CV combinations produced the lowest overall irritation scores in the present study. However, the quinolone/Mg formulations appeared superior to the quinolone/CV formulations in that two of three sites given the 16 mg/mL quinolone formulation were undetectable and none of the six quinolone/Mg sites had edema or were dark red. The $Mg^{2+}$ formulation appeared superior based on the lack of dark red lesions or edema at any of the sites and two of the six sites were undetectable internally.

Table 3 provides additional summary information about the results of this experiment.

TABLE 3

Experiment 3
Observed and summary results 0.2 mL injection sites (triplicate)

| Formulation (16 or 25 mg/mL) | Mean 48 Hr Irritation Score | Mean Internal Lesion volume cm³ | TIS | Sum of Rank Score |
|---|---|---|---|---|
| 16 CV | 3.00 | 0.23 | 9.70 | 7 |
| 25 CV | 2.67 | 0.54 | 9.63 | 8 |
| 16 Mg$^{2+}$ | 3.00 | 0.02 | 9.05 | 8 |
| 25 Mg$^{+2}$ | 2.67 | 0.29 | 8.87 | 8 |
| 16 IL | 2.67 | 0.47 | 9.35 | 10 |
| 16 CA | 3.00 | 0.74 | 11.21 | 16 |
| 25 CA | 3.00 | 1.35 | 13.04 | 19 |
| 25 IL | 3.00 | 1.41 | 13.24 | 19 |

TIS is Total Irritation Score.

Experiment 4. Four quinolone formulations (25 and 50 prepared as solutions and as suspensions) were evaluated for local tolerance when injected once subcutaneously into cattle.

Injection volumes and doses: 25 mg/mL test articles: 19.0 mL/site (approximately 1.5 mg/kg/site). 50 mg/mL test articles: 9.3 or 19 mL/site (approximately 1.5 or 3 mg/kg/site).

Formulations: The formulations are made to concentrations in solutions at 25 and 50 mg/mL of Quinolone as Free Base (QFB). Solution formulations were made by adding bulk drug to equivalent molar magnesium chloride solutions (in purified water) and stirring until completely dissolved; NaCl was added as needed to adjust tonicity. Quinolone in suspension at 25 and 50 mg/mL QFB were made by adding micronized bulk drug to the cottonseed oil vehicle. No control article was injected. Solutions were sterile filtered.

External Injection Site Evaluations. Palpable and sometimes visible swellings were detected at all subcutaneous injection sites in the necks of the cattle beginning ≧1 day postinjection (PI) and were still present 9 days PI. The 25 mg/mL QFB formulations at 19.0 caused diffuse palpable swelling within 1 to 4 days PI, which remained palpable for the rest of the study. The 50 mg/mL QFB formulations at 9.3 mL/site caused either diffuse palpable swelling (quinolone solution containing MgCl$_2$) or visible swelling (quinolone in cottonseed vehicle) at 1 day PI, which remained unchanged through study termination. The 50 mg/mL QFB solution and suspension at 19.0 mL/site caused palpable swellings at 1 day PI, which both progressed into visible swellings by 9 days PI.

Subcutaneous thoracic injection sites given 19.0 mL of the 25 mg/mL QFB solution and 9.3 and 19.0 mL of the 50 mg/mL QFB solution had no external swelling during the study. Thoracic sites given 19.0 mL of the 25 mg/mL QFB suspension and 9.3 mL of the 50 mg/mL QFB suspension had palpable or visible external swelling by 9 days PI. Thoracic sites for 2 of 3 animals given 19.0 mL of the 50 mg/mL suspension had palpable swelling by 9 days PI, but 1 animal had no detectable swelling at this site during the course of the study.

Internal Injection Site Evaluations. Lesions were present at all injection sites 9 days PI. Minimal-to-mild reactions were seen at all injection sites administered the quinolone solutions (both 25 and 50 mg/mL QFB) containing MgCl$_2$, and mild-to-severe reactions were seen at sites given the quinolone formulations in cottonseed oil vehicle. The least severe lesions were pink or plum/tan and small (classified as minimal or occasionally mild), whereas the most severe lesions (classified as moderate or severe) were plum/tan or dark red, often with edema and adhesion of the dermis to the external muscle fascia, and large. Lesion volumes tended to be similar for each formulation and volume, whether given in the neck or over the thorax, although there was some variation in color.

Tables 4A and B provides additional or summary information about the results of this experiment.

Additionally, in another study involving citrate formulations, the citrate study, data not presented here, comparisons were made with this Experiment 4. Citrate containing solutions had larger lesion volumes and greater variability in those lesion volumes when compared to the lesions from Mg containing solutions in this Experiment. Internally, all injection sites in the citrate study were either dark red or plum-colored and tan with edema at the periphery; only one site injected with the quinolone solution containing magnesium had any dark red and that was only in a small area.

TABLE 4A

Experiment 4
Observed and summary results neck injection sites (single site)

| Formulation mg/ml | Dose per site (mg/kg) | Internal Lesion volume cm³ | Severity Score | Rank |
|---|---|---|---|---|
| 25 solution | 1.5 | 11 | 1 | 1 |
| 50 solution | 1.5 | 42 | 2 | 3 |
| 50 solution | 3 | 23 | 2.5 | 2 |
| 25 suspension | 1.5 | 81 | 2.5 | 4 |
| 50 suspension | 1.5 | 228 | 3 | 6 |
| 50 suspension | 3 | 171 | 3 | 5 |

TABLE 4B

Experiment 4
Observed and summary results thorax injection sites (triplicate)

| Formulation mg/ml | Dose per site (mg/kg) | Mean Internal Lesion volume cm³ | Mean Severity Score | Rank |
|---|---|---|---|---|
| 25 solution | 1.5 | 22 ± 7 | 1 ± 0 | 2 |
| 50 solution | 1.5 | 12 ± 1 | 1.33 ± 0.47 | 1 |
| 50 solution | 3 | 25 ± 8 | 1.33 ± 0.47 | 3 |
| 25 suspension | 1.5 | 299 ± 13 | 2.67 ± 0.24 | 5 |
| 50 suspension | 1.5 | 217 ± 53 | 2.67 ± 0.24 | 4 |
| 50 suspension | 3 | 501 ± 87 | 3.33 ± 0.25 | 6 |

Experiment 5. Groups of three rats each received four formulations (with different ratios of Mg:drug) at one of three pH levels.

Formulations: Quinolone (16 mg/mL or 0.04 M) was formulated at different fixed ratios with MgCl$_2$ (1:4, 1:2, 1:1 and 2:1). Aliquots of each ratio were pH adjusted with HCl or NaOH to 5, 7 or 9; tonicity was adjusted with NaCl. Solutions were sterile filtered.

Treatment Groups: There were three treatment groups with three female rats per group, 15 weeks of age; each group received one pH level. Each rat within a group received four 0.2 mL subcutaneous injections one of each Mg:drug ratios.

Clinical and Gross Observations: Mean lesion volumes at necropsy were greatest for the formulations with a Mg:drug ratio of 1:4; lesion volumes ranged from 0.101(pH 5) to 0.334 (pH 7). Lesions were seen at 9 of the 9 1:4 formulation injection sites. Mean lesion volumes were smallest for the formulations with Mg:drug ratio 1:1; lesion volumes ranged from 0.008 (pH 5) to 0.053 (pH 7). Lesions were seen at 4 of the 9 sites given the 1:1 formulations. The 1:2 and 2:1 Mg:drug formulations had intermediate lesion volumes; lesions were seen at 7 of the 9 sites with the 1:2 formulations and 4 of the 9 sites given the 2:1 formulations. In this study, only one site a had dark red lesion and one had mild edema. Both of these sites were given the 1:2 Mg:drug formulation (pH 5 and pH 9, respectively). No evidence of epidermal/dermal necrosis was seen at any of the injection sites in this study.

Conclusion: Reduced tissue irritation of $Mg^{2+}$ formulations seen in previous studies was confirmed and only slight differences in tissue irritation were seen in the 12 formulations in the present study. The four least irritating formulations were those with 1:1 Mg:drug ratio pH 5<2:1 ratio pH 7<1:1 ratio pH 9<2:1 ratio pH 9.

Table 5 provides additional or summary information about the results of this experiment.

TABLE 5

Experiment 5
Observed and summary results (triplicate)

| Formulation ratio/pH | Mean Internal Lesion volume $cm^3$ | Severity Score | Sum Score | Sum Score by ratio |
|---|---|---|---|---|
| 2:1/5 | 0.060 ± 0.020 | 2 | 2.060 | 4.189 |
| 2:1/7 | 0.045 ± 0.015 | 1 | 1.045 | |
| 2:1/9 | 0.084 ± 0.028 | 1 | 1.084 | |
| 1:1/5 | 0.024 ± 0.008 | 1 | 1.024 | 4.242 |
| 1:1/7 | 0.159 ± 0.053 | 2 | 2.159 | |
| 1:1/9 | 0.059 ± 0.020 | 1 | 1.059 | |
| 1:2/5 | 0.107 ± 0.036 | 3 | 3.107 | 9.585 |
| 1:2/7 | 0.334 ± 0.111 | 4 | 4.334 | |
| 1:2/9 | 0.144 ± 0.048 | 2 | 2.144 | |
| 1:4/5 | 0.302 ± 0.101 | 3 | 3.302 | 21.326 |
| 1:4/7 | 1.001 ± 0.334 | 4 | 5.001 | |
| 1:4/9 | 0.438 ± 0.146 | 3 | 3.438 | |

Experiment 6. Twelve rats each received formulations (6 replicates per formulation) at higher concentrations and ratios (25 and 50 mg/mL and 2:1 and 3:1 Mg:drug ratios).

Formulations: Quinolone 25 mg/mL (0.06 M) and 50 mg/mL (0.12 M) were formulated at different fixed ratios with $MgCl_2$ (2:1 and 3:1). Bulk drug was added to the specified vehicle and dissolved with stirring; the solutions were sterile filtered.

Treatment Groups: All of the formulations were randomized over the twelve female rats, 10–15 weeks of age. Each rat received three 0.2 mL subcutaneous injections of three different formulations randomized over the four sites. (Note: Our original design was to include a total of eight formulations, however four of the planned formulations were not compatible and not used.)

Clinical and Gross Observations: External evidence of injections was present at all sites 48 hr. PI and varied from palpable swelling or discoloration to crusty or scabbed lesions (Table 6). External injections site reactions were less severe (fewer and smaller scabbed areas) at the sites injected with formulations containing 25 mg/mL premafloxacin than those containing 50 mg/mL premafloxacin.

No internal lesions were seen at the following injection sites: 3 of the 6 sites with 3:1 Mg: 25 mg/mL quinolone; 4 of the 6 sites with 2:1 Mg: 25 mg/mL; 1 of the 6 site receiving 2:1 Mg: 50 mg/mL. All six sites receiving 3:1 Mg: 50 mg/mL drug had lesions. Based on mean lesion volume and severity score, both the 3:1 and 2:1 ratio 25 mg/mL were similar and of minimal severity <2:1 ratio 50 mg/mL<3:1 50 mg/mL. Although the 3:1 50 mg/mL formulations caused the greatest reactions in this experiment, they were still less severe than the previously evaluated formulations containing citric acid. None of the internal sites injected with the 25 mg/mL formulations were dark red.

Table 6 provides additional or summary information about the results of this experiment.

TABLE 6

Experiment 6
Observed and summary results 0.2 mL injection sites (N = 6)

| Formulation (mg/mL/ratio) | Mean External Lesion Score $cm^3$ | Mean Internal Lesion volume | Total Severity Score | Sum Score |
|---|---|---|---|---|
| 25/2:1 | 2.33 | 0.08 ± 0.14 | 3 | 3.46 |
| 25/3:1 | 2.33 | 0.13 ± 0.22 | 3.5 | 4.30 |
| 50/2:1 | 2.50 | 0.56 ± 0.62 | 9 | 12.33 |
| 50/3:1 | 2.50 | 1.17 ± 0.59 | 15 | 22.00 |

Experiment 7. The determination of preliminary residue depletion profile in calves following subcutaneous administration of 14C-quinolone with and without magnesium.

Formulations: Radiolabeled quinolone was combined with unlabeled quinolone to yield solutions containing quinolone at 50 mg/mL with a specific activity of 2.25 uCi/mg. Solution 1: 4.92 g of unlabeled quinolone and 11.26 mCi 14C-quinolone were dissolved in 0.16 M HCl, the solution was titrated to pH 4–5 with 1 M NaOH and diluted with deionized water to a final volume of 100 mL. Solution 2: 4.92 g of unlabeled quinolone and 11.26 mCi 14C-quinolone were dissolved in 0.24 M $MgCl_2$—$6H_2O$ and diluted to 100 mL with deionized water.

Treatment Groups: Ten (male and female) Holstein calves approximately 50–85 kg were used. Each animal was injected with a single subcutaneous injection (approximately 0.2 mL dose solution/kg body weight). The dose level was approximately 10 mg/kg (22.5 uCi/kg) body weight. Whole blood samples (approximately 50 mL) were collected from each animal at 0.5, 1, 1.5, 2, 2.5, 3, 6, 12, 24, and 48 h after dosing or until euthanasia. Following euthanasia, fat, muscle, lung, kidney, liver and injection site tissue samples (approximately 500 g) were collected. Blood and tissue samples were combusted and drug residue determined by liquid scintillation counting.

Figure 2:
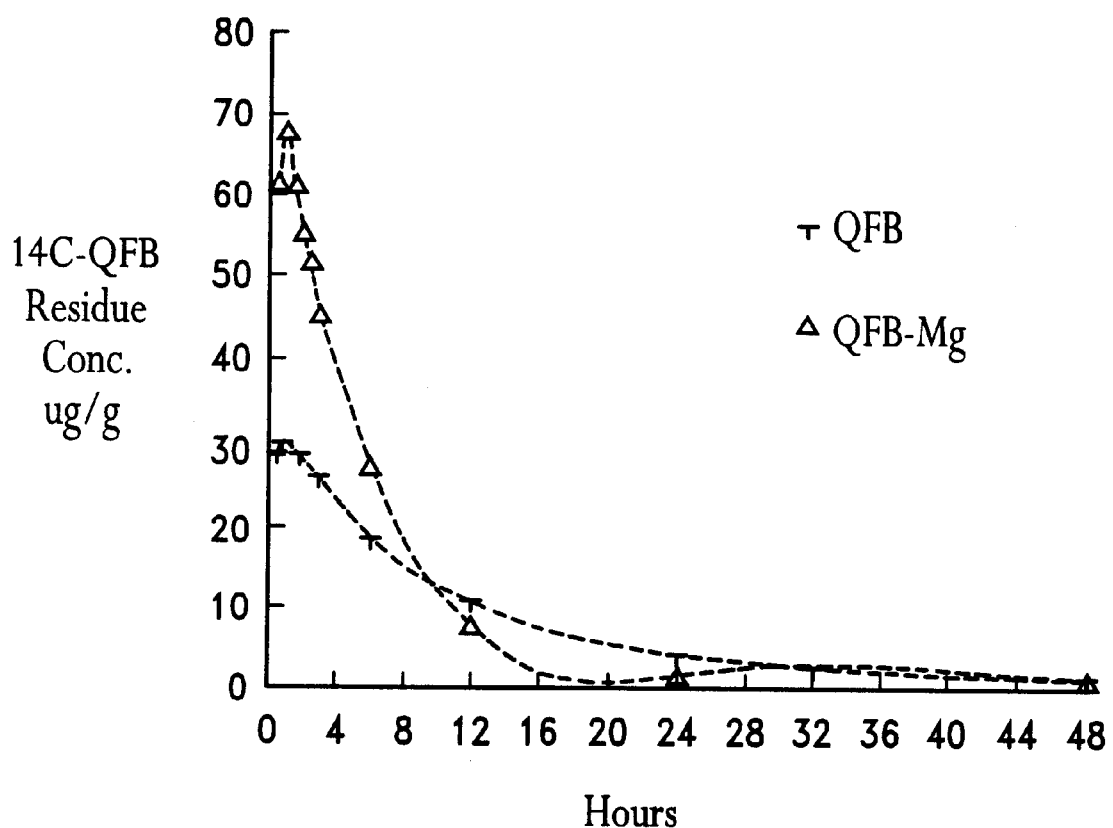
FIG. 2. Shows the serum depletion profile in two treatment groups of calves following subcutaneous administration of radiolabeled 14C-quinolone with and without magnesium.

The results of the study indicate that the formulation of 14C-quinolone with magnesium (QFB-Mg) achieves significantly higher serum levels than the same formulation without magnesium (QHB). FIGS. 1 & 2 shows the serum time profile for each of the two treatment groups. FIG. 1 shows data from time 0 to 12 hours. FIG. 2 shows the same data on a different scale from time 0 to 48 hours. As can be seen in the figures, the QFB-Mg group achieved a maximum serum concentration of 67.9 ug/mL of QFB within 1 hour of treatment, where the QFB group only achieved a serum concentration of 30.4 ug/mL at 1 hour of treatment. The decline of QFB-Mg from the serum of the bovine was also significantly faster than in the QFB group as well, with only 0.6 ug/mL remaining after 48 hours in the QFB-Mg group and 1.0 ug/mL remaining in the QFB group. Tissue levels reflect similar profiles (Table 7) with higher QFB concentration occurring in all tissues (except injection site) in the earlier sampling time points for the QFB-Mg group as compared to the QFB group and lower concentrations in the QFB-Mg group (including injection site) at the later time points.

The one exception is the injection site in which a significantly lower concentration of QFB was found in the injection site for the QFB-Mg group (2,680 ug/g) as compared to the QFB group (10,480 ug/g). This data along with the serum profiles and tissue residue data suggest that QFB is absorbed much more quickly from the injection site in the group treated with QFB-Mg as compared to the group treated with QFB.

Table 7 provides additional or summary information about the results of this experiment.

TABLE 7

Total $^{14}$C-quinolone Residues in Tissue by Euthanasia Time Expressed as µg/g

| Tissue | 3 hr | 6 hr | 12 hr | 24 hr | 48 hr |
|---|---|---|---|---|---|
| Group QFB | | | | | |
| Fat | 45.4 | 16.8 | 7.8 | 13.9 | 1.7 |
| Muscle | 50.1 | 38.4 | 24.3 | 9.4 | 1.4 |
| Lungs | 146.8 | 96.6 | 53.1 | 27.6 | 4.8 |
| Kidneys | 353.2 | 234.1 | 121.3 | 90.3 | 15.0 |
| Liver | 215.5 | 147.2 | 110.9 | 59.5 | 13.4 |
| Inj. Site | 10,482 | 12,382 | 1,737 | 932.5 | 225.7 |
| Group QFB-Mg | | | | | |
| Fat | 32.3 | 41.0 | 6.9 | 1.4 | 1.7 |
| Muscle | 106.7 | 82.5 | 14.9 | 1.7 | 0.8 |
| Lungs | 215.2 | 166.4 | 29.8 | 4.9 | 4.8 |
| Kidneys | 479.6 | 397.2 | 66.8 | 14.3 | 10.2 |
| Liver | 331.7 | 271.2 | 64.5 | 15.7 | 11.1 |
| Inj. Site | 2,683 | 3,428 | 25.8 | 9.0 | 7.4 |

What is claimed is:

1. A solution comprising an individual stereoisomer of a compound of the formula

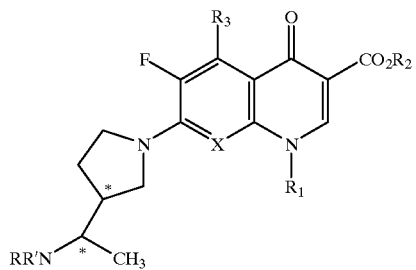

wherein

* denotes an asymmetric carbon atom;

X is C—OR;

$R_1$ is ethyl, cyclopropyl, or 2,4-difluorophenyl;

$R_2$ is hydrogen, alkyl of 1–4 carbon atoms or a cation;

$R_3$ is hydrogen, amino, or methyl;

R and R' a each independently hydrogen or alkyl of 1-carbon atoms, or pharmaceutically acceptable acid addition salt thereof in solution with Mg2+ ions, in a range from ratios of 1:4 to 3:1 parts of Mg2+ ion to stereoisomer.

2. A solution of claim 1, selected from solutions having ratios of 1:4, 1:2, 1:1, 2:1 and 3:1 ratios of Mg2+ ion to compound.

3. A solution of claim 2 where the compound is selected from the compounds comprising the compounds of Formula I, below,

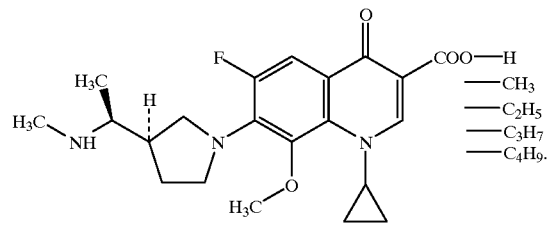

4. A solution of claim 3 where the compound is selected from 3R,1S-1-cyclopropyl-7-(3-(1-(methylamino)ethyl)-1-pyrrolidinyl)-6-fluoro-1,4-dihydro-8-methoxy-4-oxo-3-quinolinecarboxylic acid and $C_{1-4}$ carboxy esters thereof.

5. A solution of claim 4 where the compound is 3R,1S-1-cyclopropyl-7-(3-(1-(methylamino)ethyl)-1-pyrrolidinyl)-6-fluoro-1,4-dihydro-8-methoxy-4-oxo-3-quinolinecarboxylic acid.

6. A solution of claim 4 where the ratio of Mg2+ ion to compound is 1:1 or 2:1.

7. A solution of claim 5 where the ratio of Mg2+ ion to compound is 2:1.

8. A solution of 1:4 to 3:1 parts of Mg2+ ion to an individual stereoisomer of a compound of the formula

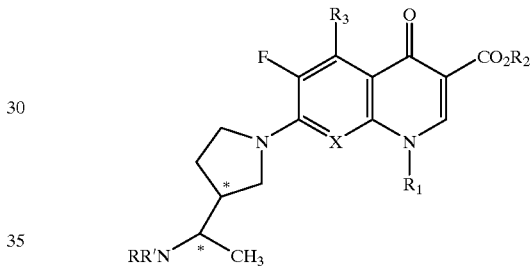

wherein

* denotes an asymmetric carbon atom;

X is C—OR;

$R_1$ is ethyl, cyclopropyl, or 2,4-difluorophenyl;

$R_2$ is hydrogen, alkyl of 1–4 carbon atoms or a cation;

$R_3$ is hydrogen, amino, or methyl;

R and R' are each independently hydrogen or alkyl of 1-carbon atoms, or a pharmaceutically acceptable acid addition salt thereof produced as a result of mixing the stereoisomer in water and MgCl$_2$.

9. A solution of claim 6 were the compound is first mixed with water before the MgCl$_2$ is added to the solution.

10. A solution of claim 8, where the ratio of Mg2+ ion to compound, is 2:1 parts of Mg2+ ion to compound, where the compound is a quinolone and where the quinolone is 3R,1S-1-cyclopropyl-7-(3(1-(methylamino)ethyl)-1-pyrrolidinyl)-6-fluoro-1,4-dihydro-8-methoxy-4-oxo-3-quinolinecarboxylic acid.

11. A solution of claim 7, where the solution is agitated or mixed until there is no precipitated quinolone.

12. A solution of claim 10, where the pH of the solution is between about 6.0 and 8.0.

13. A solution of claim 12, where the pH of the solution is between about 6.5 and 7.5.

14. A solution of claim 4, where the $C_{1-4}$ carboxy ester is the ethyl ester.

15. A solution of claim 4 where the $C_{1-4}$ carboxy ester is the methyl ester.

* * * * *